(12) United States Patent  
Boehringer et al.

(10) Patent No.: US 7,417,144 B2  
(45) Date of Patent: Aug. 26, 2008

(54) FACTOR XA INHIBITORS

(75) Inventors: Markus Boehringer, Moehlin (CH); Katrin Groebke Zbinden, Liestal (CH); Wolfgang Haap, Loerrach (DE); Hans Hilpert, Muenchenstein (CH); Narendra Panday, Basel (CH); Fabienne Ricklin, Hombourg (FR)

(73) Assignee: Hoffman-La Roche Inc., Nutley, NJ (US)

( * ) Notice: Subject to any disclaimer, the term of this patent is extended or adjusted under 35 U.S.C. 154(b) by 0 days.

(21) Appl. No.: 11/482,441

(22) Filed: Jul. 7, 2006

(65) Prior Publication Data  
US 2007/0015812 A1   Jan. 18, 2007

(30) Foreign Application Priority Data  
Jul. 15, 2005   (EP)   ................... 05106542

(51) Int. Cl.  
*A61K 31/5375* (2006.01)

(52) U.S. Cl. .................... 544/173; 514/230.8

(58) Field of Classification Search ............... 544/173; 514/230.8  
See application file for complete search history.

(56) References Cited  
U.S. PATENT DOCUMENTS  
6,642,228 B1   11/2003   Hayashi et al.  
2002/0193399 A1   12/2002   Lin et al.

FOREIGN PATENT DOCUMENTS

| DE | 199 00 471 A1 | 7/2000 |
|----|----|----|
| WO | WO 98/35957 | 8/1998 |
| WO | WO 00/78716 | 12/2000 |
| WO | WO 01/51484 A1 | 7/2001 |
| WO | WO 02/096873 | 12/2002 |
| WO | WO 03/045912 | 6/2003 |
| WO | WO 03/063797 | 8/2003 |
| WO | WO 2004/082687 | 9/2004 |
| WO | WO 2005/032472 | 4/2005 |

OTHER PUBLICATIONS

Lottenberg et al., Biochem. Biophys. Acta, 742, pp. 539-557 (1983).  
Eadie, G.S., J. Biol. Chem., 146, pp. 85-93 (1942).

*Primary Examiner*—Rebecca L Anderson  
*Assistant Examiner*—Robert Havlin  
(74) *Attorney, Agent, or Firm*—George W. Johnston; Dennis P. Tramaloni; Brian C. Remy

(57) ABSTRACT

The invention is concerned with novel heteroaryl fused cyclic amines of formula (I)

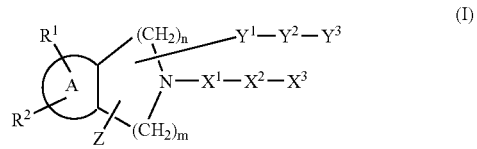

wherein A, $X^1$ to $X^3$, $Y^1$ to $Y^3$, Z, $R^1$, $R^2$, m and n are as defined in the description and in the claims, as well as physiologically acceptable salts thereof. These compounds inhibit coagulation factor Xa and can be used as medicaments.

20 Claims, No Drawings

FACTOR XA INHIBITORS

PRIORITY TO RELATED APPLICATIONS

This application claims the benefit of European Application No. 05106542.3, filed Jul. 15, 2005, which is hereby incorporated by reference in its entirety.

The invention is concerned with novel Factor Xa inhibitors that are heteroaryl fused cyclic amines of formula (I),

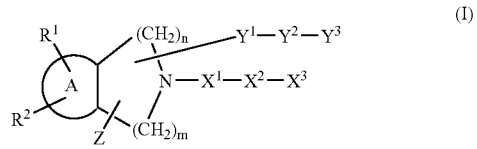

wherein
A heteroaryl;
$R^1$ and $R^2$
are independently hydrogen, $C_{1-6}$ alkyl, $C_{1-6}$ alkoxy, fluoro $C_{1-6}$ alkoxy, hydroxy $C_{1-6}$ alkoxy, $C_{1-6}$ alkoxy $C_{1-6}$ alkoxy, mono or di $C_{1-6}$ alkyl substituted amino $C_{1-6}$ alkoxy, halogen, cyano, nitro, —N(R')—CO—($C_{1-6}$ alkyl optionally substituted by one or more fluorine atoms) wherein R' is hydrogen, $C_{1-6}$ alkyl or fluoro $C_{1-6}$ alkyl, —N(R')—CO—O— ($C_{1-6}$ alkyl optionally substituted by one or more fluorine atoms) wherein R' is hydrogen, $C_{1-6}$ alkyl or fluoro $C_{1-6}$ alkyl, —N(R')—CO—N(R") (R''') wherein R', R" and R''' are independently hydrogen, $C_{1-6}$ alkyl or fluoro $C_{1-6}$ alkyl, or —N(R')—$SO_2$—($C_{1-6}$ alkyl optionally substituted by one or more fluorine atoms) wherein R' is hydrogen, $C_{1-6}$ alkyl or fluoro $C_{1-6}$ alkyl;
or $R^1$ and $R^2$
are independently —$SO_2$—N(R')(R"), —C(O)—N(R')(R") or —N(R')(R") wherein R' and R" are independently hydrogen, $C_{1-6}$ alkyl or fluoro $C_{1-6}$ alkyl or R' and R", together with the nitrogen atom to which they are attached, form heterocycyl;
$X^1$ is —C(O)—($C_{0-6}$ alkylene)-$NR^3$—($C_{0-6}$ alkylene)-, —($C_{0-6}$ alkylene)-C(O)—$NR^3$—($C_{0-6}$ alkylene)-, —($C_{1-6}$ alkylene)-$NR^3$—C(O)—($C_{0-6}$ alkylene)-, —C(O)—($C_{0-6}$ alkylene)-, $C_{0-6}$ alkylene, —$SO_2$—($C_{0-6}$ alkylene)-, —($C_{0-6}$ alkylene)-$SO_2$—$NR^3$—($C_{0-6}$ alkylene)- or

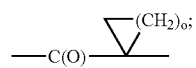

$X^2$ is arylene, heteroarylene or heterocyclylene, wherein the arylene, heteroarylene and heterocyclylene may be optionally independently substituted by one or more of $C_{1-6}$ alkyl, $C_{1-6}$ alkoxy, halogen, cyano, nitro, amino, —N(R')—CO—($C_{1-6}$ alkyl optionally substituted by one or more fluorine atoms) wherein R' is hydrogen, $C_{1-6}$ alkyl or fluoro $C_{1-6}$ alkyl, —N(R')—CO—O—($C_{1-6}$ alkyl optionally substituted by one or more fluorine atoms) wherein R' is hydrogen, $C_{1-6}$ alkyl or fluoro $C_{1-6}$ alkyl, —N(R')—CO—N(R") (R''') wherein R', R" and R''' are independently hydrogen, $C_{1-6}$ alkyl or fluoro $C_{1-6}$ alkyl, —C(O)—N(R')(R") wherein R' and R" are independently hydrogen, $C_{1-6}$ alkyl or fluoro $C_{1-6}$ alkyl, or R' and R", together with the nitrogen atom to which they are attached, form heterocycyl, —NR'R" wherein R' and R" are independently hydrogen, $C_{1-6}$ alkyl or fluoro $C_{1-6}$ alkyl, or R' and R", together with the nitrogen atom to which they are attached, form heterocycyl,

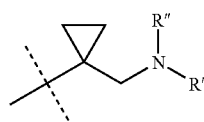

wherein R' and R" are independently $C_{1-6}$ alkyl or fluoro $C_{1-6}$ alkyl, or R' and R", together with the nitrogen atom to which they are attached, form heterocyclyl,

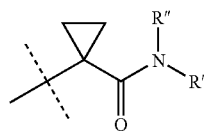

wherein R' and R" are independently $C_{1-6}$ alkyl or fluoro $C_{1-6}$ alkyl, or R' and R", together with the nitrogen atom to which they are attached, form heterocyclyl,

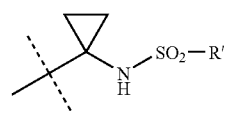

wherein R' is fluoro $C_{1-6}$ alkyl or

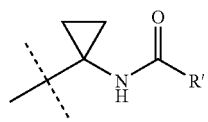

wherein R' is fluoro $C_{1-6}$ alkyl, wherein one or two carbon atoms of the arylene, heteroarylene or heterocyclylene may be optionally replaced with a carbonyl group;
$X^3$ is hydrogen, aryl, heteroaryl or heterocyclyl, where the aryl, heteroaryl and heterocyclyl may be optionally independently substituted by one or more of $C_{1-6}$ alkyl, $C_{1-6}$ alkoxy, halogen, cyano, nitro, amino, mono-$C_{1-6}$ alkyl substituted amino, di-$C_{1-6}$ alkyl substituted amino, mono-$C_{1-6}$ alkyl substituted amino-$C_{1-6}$ alkyl, di-$C_{1-6}$ alkyl substituted amino-$C_{1-6}$ alkyl, —$SO_2$—$C_{1-6}$ alkyl, —$SO_2$—$NH_2$, —$SO_2$—NH—$C_{1-6}$ alkyl or —$SO_2$—N($C_{1-6}$ alkyl)$_2$,
wherein one or two carbon atoms of the aryl, heteroaryl and heterocyclyl may be optionally replaced with a carbonyl group;
$R^3$ is hydrogen or $C_{1-6}$ alkyl;
$Y^1$ is —($C_{0-6}$ alkylene)-C(O)—$NR^3$—($C_{0-6}$ alkylene)-, —($C_{0-6}$ alkylene)-$NR^3$—C(O)—($C_{0-6}$ alkylene)- or $C_{0-6}$ alkylene;
$Y^2$ is arylene, heteroarylene or heterocyclylene, wherein the arylene, heteroarylene and heterocyclylene may be optionally independently substituted by one or more of $C_{1-6}$ alkyl, $C_{1-6}$ alkoxy, halogen, cyano, nitro, amino, —N(R')—CO—($C_{1-6}$ alkyl optionally substituted by one or more fluorine atoms) wherein R' is hydrogen, $C_{1-6}$ alkyl or fluoro $C_{1-6}$ alkyl, —N(R')—CO—O—($C_{1-6}$ alkyl optionally substituted by one or more fluorine atoms) wherein R' is hydrogen, $C_{1-6}$ alkyl or fluoro $C_{1-6}$ alkyl, —N(R')—CO—N(R")(R''') wherein R', R" and R''' are independently hydrogen, $C_{1-6}$ alkyl or fluoro $C_{1-6}$ alkyl, —C(O)—N(R')(R") wherein R' and R" are independently hydrogen, $C_{1-6}$ alkyl or halo $C_{1-6}$ alkyl, or R' and R", together with the nitrogen atom to which they are attached, form heterocycyl, —NR'R" wherein R' and R" are independently hydrogen, $C_{1-6}$ alkyl or halo $C_{1-6}$ alkyl, or R' and R", together with the nitrogen atom to which they are attached, form heterocycyl,

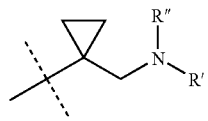

wherein R' and R" are independently $C_{1-6}$ alkyl or fluoro $C_{1-6}$ alkyl, or wherein R' and R", together with the nitrogen atom to which they are attached, form heterocyclyl,

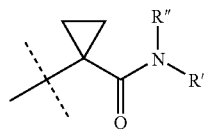

wherein R' and R" are independently $C_{1-6}$ alkyl or fluoro $C_{1-6}$ alkyl, or wherein R' and R", together with the nitrogen atom to which they are attached, form heterocyclyl,

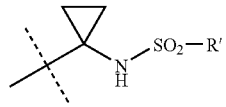

wherein R' is fluoro $C_{1-6}$ alkyl or

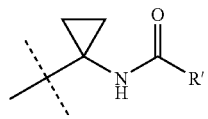

wherein R' is $C_{1-6}$ alkyl, wherein one or two carbon atoms of the arylene, heteroarylene or heterocyclylene may be optionally replaced with a carbonyl group;

$Y^3$ is hydrogen, aryl, heteroaryl or heterocyclyl, wherein the aryl, heteroaryl and heterocyclyl may be optionally indepenently substituted by one or more of $C_{1-6}$ alkyl, $C_{1-6}$ alkoxy, halogen, cyano, nitro, amino, mono-$C_{1-6}$ alkyl substituted amino, di-$C_{1-6}$ alkyl substituted amino, mono-$C_{1-6}$ alkyl substituted amino-$C_{1-6}$ alkyl, di-$C_{1-6}$ alkyl substituted amino-$C_{1-6}$ alkyl, —$SO_2$—$C_{1-6}$ alkyl, —$SO_2$—$NH_2$, —$SO_2$—NH—$C_{1-6}$ alkyl or —$SO_2$—N($C_{1-6}$ alkyl)$_2$, wherein one or two carbon atoms of the aryl, heteroaryl and heterocyclyl may be optionally replaced with a carbonyl group;

Z is attached to the same carbon atom as —$Y^1$—$Y^2$—$Y^3$, and is hydrogen or $C_{1-6}$ alkyl;

n is 0, 1 or 2;

m is 0, 1 or 2;

m+n is 2 or 3;

o is an integer from 1 to 5;

and prodrugs and pharmaceutically acceptable salts thereof.

Further, the invention is concerned with processes and intermediates for the manufacture of the above compounds, pharmaceutical preparations which contain such compounds, the use of these compounds for the production of pharmaceutical preparations as well as processes for the manufacture of intermediates.

The compounds of formula (I) are active compounds that inhibit coagulation factor Xa. These compounds consequently can influence blood coagulation. They inhibit the formation of thrombin and can be used for the treatment and/or prevention of thrombotic disorders, such as, arterial and venous thrombosis, deep vein thrombosis, peripheral arterial occlusive disease (PAOD), unstable angina pectoris, myocardial infarction, coronary artery disease, pulmonary embolism, stroke (cerebral thrombosis) due to atrial fibrillation, inflammation and arteriosclerosis. They have potential benefit in the treatment of acute vessel closure associated with thrombolytic therapy and restenosis, e.g. after transluminal coronary angioplasty (PTCA) or bypass grafting of the coronary or peripheral arteries and in the maintenance of vascular access patency in long term hemodialysis patients. Factor Xa inhibitors of this invention may form part of a combination therapy with an anticoagulant with a different mode of action or with a platelet aggregation inhibitor or with a thrombolytic agent. Furthermore, these compounds have an effect on tumour cells and prevent metastases. They can therefore also be used as antitumour agents.

Other inhibitors of factor Xa had previously been suggested for the inhibition of the formation of thrombin and for the treatment of related diseases. However, there is still a need for novel factor Xa inhibitors which exhibit improved pharmacological properties, e.g. an improved selectivity towards thrombin.

The present invention provides novel compounds of formula (I) which are factor Xa inhibitors. The compounds of the present invention unexpectedly inhibit coagulation factor Xa and also exhibit improved pharmacological properties compared to other compounds already known in the art.

Unless otherwise indicated, the following definitions are set forth to illustrate and define the meaning and scope of the various terms used to describe the invention herein.

The term "halogen" or "halo" means fluorine, chlorine, bromine and iodine, with fluorine, chlorine and bromine being preferred, and fluorine and chlorine being more preferred.

The term "$C_{1-6}$ alkyl", alone or in combination with other groups, means a branched or straight-chain monovalent alkyl radical, having one to six carbon atoms. This term is further exemplified by such radicals as methyl, ethyl, n-propyl, isopropyl, n-butyl, s-butyl, t-butyl. $C_{1-4}$ alkyl is more preferred.

The term "$C_{0-6}$ alkylene" means a linear saturated divalent hydrocarbon radical of one to six carbon atoms or a branched divalent hydrocarbon radical of three to six carbon atoms or a bond when C is 0, e.g., methylene, ethylene, 2,2-dimethylethylene, propylene.

The term "C$_{1-6}$ alkoxy", alone or in combination with other groups, means the group R'—O—, wherein R' is a C$_{1-6}$ alkyl.

The term "hydroxy C$_{1-6}$ alkoxy" means C$_{1-6}$ alkoxy substituted by one or more hydroxy group.

The term "fluoro C$_{1-6}$ alkyl" or "fluoro C$_{1-6}$ alkoxy" means C$_{1-6}$ alkyl or C$_{1-6}$ alkoxy substituted by one or more fluorine atoms, preferably one to three fluorine atoms.

The term "aryl" means phenyl or naphthyl. Phenyl is preferred.

The term "arylene", alone or in combination with other groups, means a divalent aryl group as defined above. 1,4-phenylene is preferred.

The term "heterocyclyl", alone or combination with other groups, means non-aromatic mono- or bi-cyclic radicals of three to eight ring atoms in which one or two ring atoms are heteroatoms selected from N, O, or S(O)$_n$ (where n is an integer from 0 to 2), the remaining ring atoms being C. Monocyclic radicals are preferred.

The term "heterocyclylene", alone or combination with other groups, means a divalent heterocyclyl group as defined above.

The term "heteroaryl", alone or combination with other groups, means a monocyclic or bicyclic aromatic radical of 5 to 12 ring atoms, containing one, two, or three ring heteroatoms selected from N, O, and S, the remaining ring atoms being C, one or two carbon atoms of said ring being optionally replaced with a carbonyl group, with the understanding that the attachment point of the heteroaryl radical will be on an aromatic ring. Monocyclic radicals are preferred.

The term "heteroarylene", alone or combination with other groups, means a divalent heteroaryl group as defined above.

The term "bicyclic aromatic ring" or "bicyclic aromatic radical" contains both an aromatic monocyclic ring fused by another aromatic monocyclic ring and an aromatic monocyclic ring fused by a non-aromatic monocyclic ring. When the term "bicyclic aromatic ring" or "bicyclic aromatic radical" is used in the context of the definition of "heteroaryl" or "heteroaryl ring", at least one heteroatom must exist in the aromatic ring as a ring member. When the heteroaryl ring as A ring in formula I is a bicyclic aromatic ring, and this bicyclic aromatic ring is an aromatic monocyclic ring fused by a non-aromatic monocyclic ring, then the aromatic ring is directly fused to the nitrogen containing ring to which —Y$^1$—Y$^2$—Y$^3$, —X$^1$—X$^2$—X$^3$ and Z are attached.

Preferred radicals for the chemical groups whose definitions are given above are those specifically exemplified in Examples.

Compounds of formula (I) can form pharmaceutically acceptable acid addition salts. Examples of such pharmaceutically acceptable salts are salts of compounds of formula (I) with physiologically compatible mineral acids, such as hydrochloric acid, sulphuric acid, sulphurous acid or phosphoric acid; or with organic acids, such as methanesulphonic acid, p-toluenesulphonic acid, acetic acid, lactic acid, trifluoroacetic acid, citric acid, fumaric acid, maleic acid, tartaric acid, succinic acid or salicylic acid. The term "pharmaceutically acceptable salts" refers to such salts. Compounds of formula (I) in which a COOH group is present can further form salts with bases. Examples of such salts are alkaline, earth-alkaline and ammonium salts such as e.g. Na—, K—, Ca— and trimethylammoniumsalt. The term "pharmaceutically acceptable salts" also refers to such salts. Acid addition salts as described above are preferred.

"Optional" or "optionally" means that the subsequently described event or circumstance may but need not occur, and that the description includes instances where the event or circumstance occurs and instances in which it does not. For example, "aryl group optionally substituted with an alkyl group" means that the alkyl may but need not be present, and the description includes situations where the aryl group is substituted with an alkyl group and situations where the aryl group is not substituted with the alkyl group.

"Optionally independently substituted by one or more of" means that the group referred to may or may not be substituted, and if substituted, may be substituted by one or more other groups that may be the same or different, or several may be the same and the other or others different.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

Compounds that have the same molecular Formula but differ in the nature or sequence of bonding of their atoms or the arrangement of their atoms in space are termed "isomers." Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, if a carbon atom is bonded to four different groups, a pair of enantiomers is possible. An enantiomer can be characterized by the absolute configuration of its asymmetric center and is described by the R- and S-sequencing rules of Cahn, Ingold and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds of formula (I) can possess one or more asymmetric centers. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see discussion in Chapter 4 of "Advanced Organic Chemistry", 4th edition J. March, John Wiley and Sons, New York, 1992).

While the broadest definition of this invention is described before, certain compounds of formula (I) are preferred.

A preferred compound of the invention is a compound of formula (I) wherein A is a heteroaryl ring which is a monocyclic aromatic ring of 5 or 6 ring atoms, containing one or two, preferably two ring nitrogen atoms.

Another preferred compound of the invention is a compound of formula (I) which is

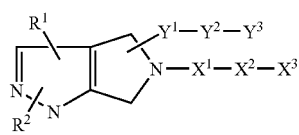

(Id)

wherein X$^1$, X$^2$, X$^3$, Y$^1$, Y$^2$, Y$^3$, R$^1$ and R$^2$ are as defined before, and wherein —Y$^1$—Y$^2$—Y$^3$ is preferably located at 4 position of the pyrrolopyrazole ring.

Another preferred compound of the invention is a compound of formula (I) wherein $X^1$ is —C(O)—NH—, —C(O)—($C_{0-6}$ alkylene)-, $C_{0-6}$ alkylene,

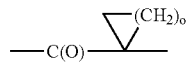

or —$SO_2$—, preferably —C(O)—NH— or —C(O)—($C_{0-6}$ alkylene)-, more preferably —C(O)—NH— or —C(O)—, especially —C(O)—NH—.

Another preferred compound of the invention is a compound of formula (I) wherein $X^2$ is arylene or heteroarylene, where the arylene and heteroarylene may be optionally independently substituted by one or more of $C_{1-6}$ alkoxy and halogen, and $X^3$ is hydrogen. Preferably —$X^2$—$X^3$ forms phenyl or pyridyl, where the phenyl and pyridyl may be optionally substituted by one or more of the same or different halogen atoms. More preferably —$X^2$—$X^3$ forms 4-chlorophenyl or 5-chloropyridyn-2-yl.

Another preferred compound of the invention is a compound of formula (I) wherein $Y^1$ is —($C_{0-6}$ alkylene)-C(O)—$NR^3$—($C_{0-6}$ alkylene)-, preferably —C(O)—$NR^3$— in which $R^3$ is as defined before, more preferably —C(O)—NH—.

Another preferred compound of the invention is a compound of formula (I) wherein $Y^2$ is 1,4-phenylene optionally substituted by one or more same or different halogen atoms, preferably 1,4-phenylene optionally substituted by one or more fluorine atoms, more preferably 2-fluoro-1,4 phenylene.

Another preferred compound of the invention is a compound of formula (I) wherein $Y^3$ is heteroaryl optionally independently substituted by one or more of $C_{1-6}$ alkyl, $C_{1-6}$ alkoxy, halogen, cyano, nitro, amino, mono-$C_{1-6}$ alkyl substituted amino, di-$C_{1-6}$ alkyl substituted amino, mono-$C_{1-6}$ alkyl substituted amino-$C_{1-6}$ alkyl, di-$C_{1-6}$ alkyl substituted amino-$C_{1-6}$ alkyl, —$SO_2$—$C_{1-6}$ alkyl, —$SO_2$—$NH_2$, —$SO_2$—NH—$C_{1-6}$ alkyl or —$SO_2$—N($C_{1-6}$ alkyl)$_2$, wherein one or two carbon atoms of the heteroaryl may be optionally replaced with a carbonyl group. Preferably $Y^3$ is unsubstituted heteroaryl which is a monocyclic aromatic ring of 5 or 6 ring atoms, containing one or two, preferably one ring nitrogen atom, wherein one carbon atom of the heteroaryl may be optionally replaced with a carbonyl group. Preferably the ring nitrogen atom of the heteroaryl is directly attached to $Y^2$, and one of the ring carbon atoms next to the ring nitrogen atom is replaced with a carbonyl group. $Y^3$ is especially 2-oxo-2H-pyridyn-1-yl.

Another preferred compound of the invention is a compound of formula (I) wherein one of $R^1$ and $R^2$ is hydrogen, and the other is $C_{1-6}$ alkyl.

Another preferred compound of the invention is a compound of formula (I) wherein Z is hydrogen.

Another preferred compound of the invention is a compound of formula (I) which is

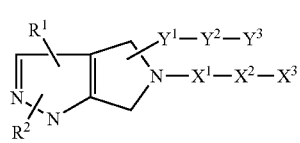

(Id)

wherein $X^1$, $X^2$, $X^3$, $Y^1$, $Y^2$ and $Y^3$ are as defined in ii) to vii), one of $R^1$ and $R^2$ is hydrogen and the other is $C_{1-6}$ alkyl, e.g.methyl, and at 1 position of the pyrrolopyrazole ring. —$Y^1$—$Y^2$—$Y^3$ is preferably located at 4 position of the pyrrolopyrazole ring.

Particularly preferred compounds of the present invention are:

(R)-1-Methyl-4,6-dihydro-1H-pyrrolo[3,4-c]pyrazole-4,5-dicarboxylic acid 5-[(4-chloro-phenyl)-amide]4-{[2-fluoro-4-(2-oxo-2H-pyridin-1-yl)-phenyl]-amide}, (R)-1-Methyl-4,6-dihydro-1H-pyrrolo[3,4-c]pyrazole-4,5-dicarboxylic acid 5-[(4-chloro-phenyl)-amide]4-{[4-(2-oxo-2H-pyrazin-1-yl)-phenyl]-amide}, (R)-1-Methyl-4,6-dihydro-1H-pyrrolo[3,4-c]pyrazole-4,5-dicarboxylic acid 5-[(4-chloro-phenyl)-amide]4-{[2-fluoro-4-(2-oxo-2H-pyrazin-1-yl)-phenyl]-amide}, (R)-1-Methyl-4,6-dihydro-1H-pyrrolo[3,4-c]pyrazole-4,5-dicarboxylic acid 5-[(4-chloro-phenyl)-amide]4-{[4-(2-oxo-2H-pyridin-1-yl)-phenyl]-amide}, (R)-1-Methyl-4,6-dihydro-1H-pyrrolo[3,4-c]pyrazole-4,5-dicarboxylic acid 5-[(4-chloro-phenyl)-amide]4-{[2,6-difluoro-4-(2-oxo-2H-pyridin-1-yl)-phenyl]-amide}.

The compounds of the present invention can be prepared, for example, by the general synthetic procedures described below.

General Synthetic Procedures
Abbreviations
AcOEt: Ethyl acetate
$Boc_2O$: Di-tert-butyl-dicarbonate
BOP: Benzotriazolyl-N-oxy-tris(dimethylamino)-phosphonium hexafluorophosphate
BOPCl: Bis-(2-oxo-3-oxazolidinyl)-phosphinic acid chloride
tBuOMe: t-Butyldimethylether
DIPEA: Diisopropyl ethyl amine
DMA: N,N-Dimethylacetamide
DMAP: 4-Dimethylaminopyridine
DME: 1,2-Dimethoxyethane
DMF: N,N-Dimethylformamide
DMSO: Dimethylsulfoxide
EDCI: N-(3-Dimetylaminopropyl)-N'-ethyl-carbodiimide hydrochloride
HATU: 1-[Bis(dimethylamino)methylene]-1H-1,2,3-triazolo[4,5-b]pyridinium 3-oxide, hexa-fluorophosphate
HOBT: 1-Hydroxybenzotriazole
MeOH: Methanol
TEA: Triethylamine
TFA: Trifluoroacetic acid
THF: Tetrahydrofuran General Procedures
Amidation: The intermediate carboxylic acid is reacted with an amine $H_2NY^2Y^3$ in a suitable solvent such as $CH_2Cl_2$, DMF, acetonitrile, THF. Activation is effected by an amide coupling reagent such as BOP, BOP-Cl, HATU/HOBT, EDCI/DMAP in the presence of a base like TEA, DIPEA, N-methylmorpholine etc. at 0° C. to 50° C. Reaction times ranged from 1 hr-72 hrs. Preferred conditions are DMF, BOPCl and DIPEA.

Deprotection: The intermediate is treated with a mineral acid such as HCl, HBr, $H_2SO_4$ or $H_3PO_4$ or a carbonic acid, in a solvent such as $CH_2Cl_2$, dioxane or HOAc at 0 to 60° C. Preferred conditions are 4N HCl in dioxane.

Acylation: The intermediate is reacted with a substituted phenyl isocyanate in a suitable solvent such as DMF, DMSO, THF at 0 to 120° C. Preferred conditions are DMF at 80° C.,

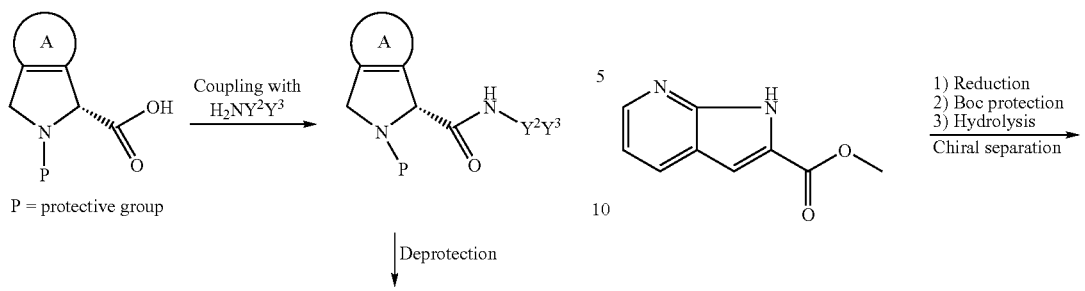
P = protective group
A, X², X³, Y² and Y³ are as defined before.
Dihydropyrrolopyrazole Derivatives
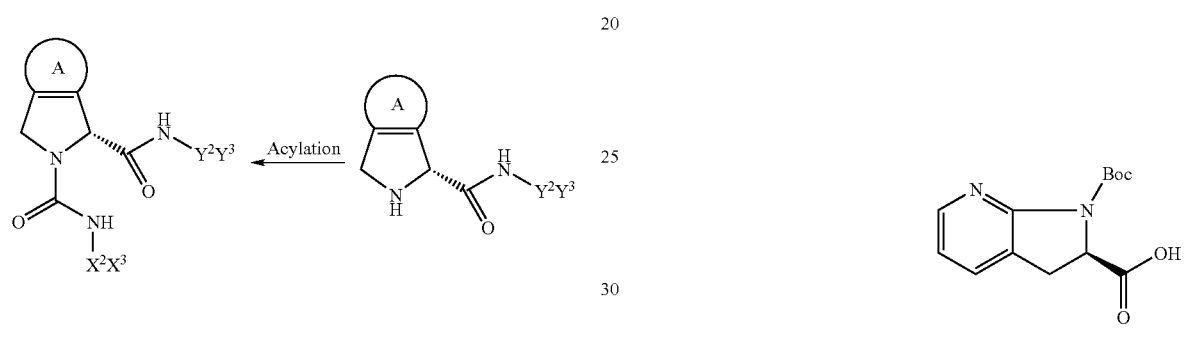
P = protective group
R¹, R², X², X³, Y² and Y³ are as defined before.
Azaindoline Derivatives
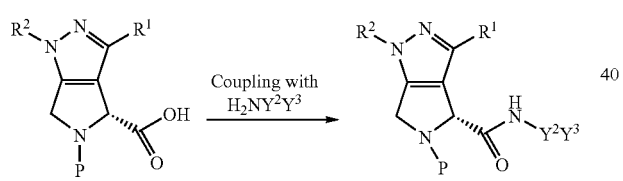
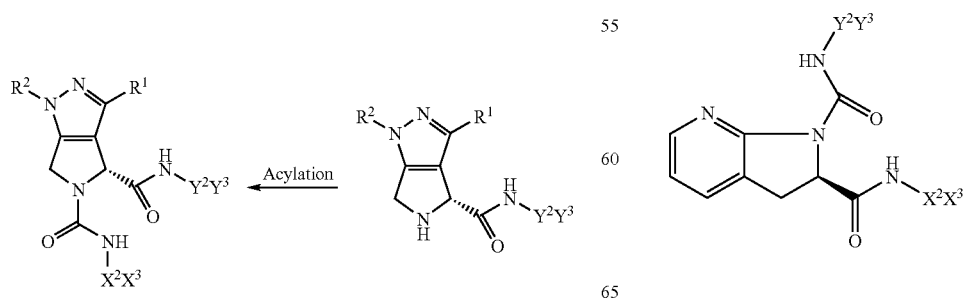
X², X³, Y² and Y³ are as defined before.

Azatetrahydroisoquinoline Derivatives

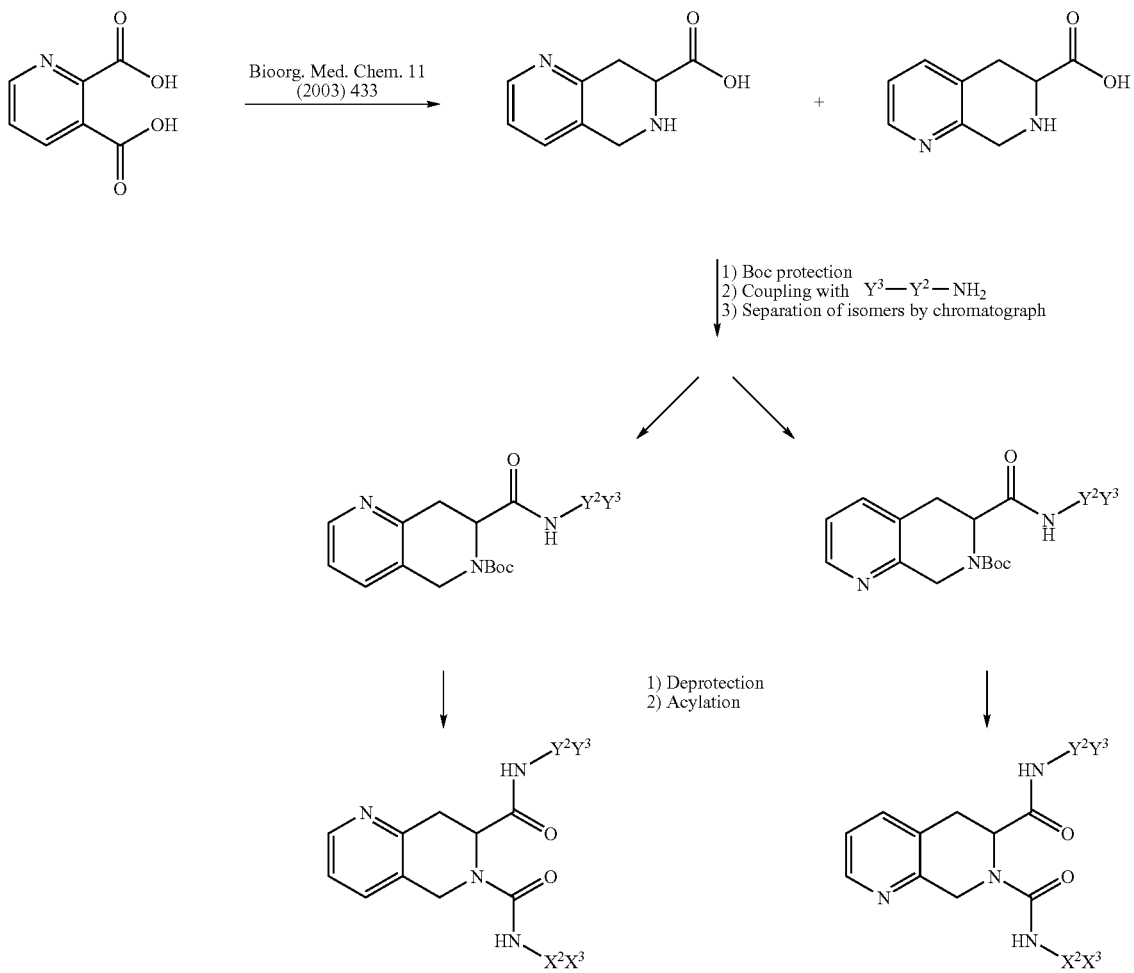

$X^2$, $X^3$, $Y^2$ and $Y^3$ are as defined before.

As described above, the compounds of formula (I) are active compounds and inhibit coagulation factor Xa. These compounds consequently influence both platelet activation which is induced by this factor and plasmatic blood coagulation. They therefore inhibit the formation of thrombi and can be used for the treatment and/or prevention of thrombotic disorders, such as, amongst others, arterial and venous thrombosis, deep vein thrombosis, peripheral arterial occlusive disease (PAOD), unstable angina pectoris, myocardial infarction, coronary artery disease, pulmonary embolism, stroke (cerebral thrombosis) due to atrial fibrillation, inflammation and arteriosclerosis. The compounds of the present invention can also be used in the treatment of acute vessel closure associated with thrombolytic therapy and restenosis, e.g. after transluminal coronary angioplasty (PTCA) or bypass grafting of the coronary or peripheral arteries and in the maintenance of vascular access patency in long term hemodialysis patients. F.Xa inhibitors of this invention may form part of a combination therapy with an anticoagulant with a different mode of action or with a platelet aggregation inhibitor or with a thrombolytic agent. Furthermore, these compounds have an effect on tumour cells and prevent metastases. They can therefore also be used as antitumour agents.

Prevention and/or treatment of thrombotic disorders, particularly arterial or deep vein thrombosis, is the preferred indication.

The invention therefore also relates to pharmaceutical compositions comprising a compound as defined above and a pharmaceutically acceptable excipient.

The invention likewise embraces compounds as described above for use as therapeutically active substances, especially as therapeutically active substances for the treatment and/or prophylaxis of diseases which are associated with the coagulation factor Xa, particularly as therapeutically active substances for the treatment and/or prophylaxis of thrombotic disorders, arterial thrombosis, venous thrombosis, deep vein thrombosis, peripheral arterial occlusive disease, unstable angina pectoris, myocardial infarction, coronary artery disease, pulmonary embolism, stroke due to atrial fibrillation, inflammation, arteriosclerosis, acute vessel closure associated with thrombolytic therapy or restenosis, and/or tumour.

In another preferred embodiment, the invention relates to a method for the therapeutic and/or prophylactic treatment of diseases which are associated with the coagulation factor Xa, particularly for the therapeutic and/or prophylactic treatment of thrombotic disorders, arterial thrombosis, venous thrombosis, deep vein thrombosis, peripheral arterial occlusive disease, unstable angina pectoris, myocardial infarction, coronary artery disease, pulmonary embolism, stroke due to atrial fibrillation, inflammation, arteriosclerosis, acute vessel closure associated with thrombolytic therapy or restenosis, and/or tumour, which method comprises administering a compound as defined above to a human being or animal.

The invention also embraces the use of compounds as defined above for the therapeutic and/or prophylactic treatment of diseases which are associated with the coagulation factor Xa, particularly for the therapeutic and/or prophylactic treatment of thrombotic disorders, arterial thrombosis, venous thrombosis, deep vein thrombosis, peripheral arterial occlusive disease, unstable angina pectoris, myocardial infarction, coronary artery disease, pulmonary embolism, stroke due to atrial fibrillation, inflammation, arteriosclerosis, acute vessel closure associated with thrombolytic therapy or restenosis, and/or tumour.

The invention also relates to the use of compounds as described above for the preparation of medicaments for the therapeutic and/or prophylactic treatment of diseases which are asscociated with coagulation factor Xa, particularly for the therapeutic and/or prophylactic treatment of thrombotic disorders, arterial thrombosis, venous thrombosis, deep vein thrombosis, peripheral arterial occlusive disease, unstable angina pectoris, myocardial infarction, coronary artery disease, pulmonary embolism, stroke due to atrial fibrillation, inflammation, arteriosclerosis, acute vessel closure associated with thrombolytic therapy or restenosis, and/or tumour. Such medicaments comprise a compound as described above.

The invention also relates to processes and the intermediates for manufacturing the compounds of formula (I) as well as processes for manufacturing the intermediates.

The inhibition of coagulation factor Xa by the compounds of the present invention can be demonstrated with the aid of a chromogenic peptide substrate assay as described hereinafter.

The compounds of formula (I) and/or their pharmaceutically acceptable salts can be used as medicaments, e.g. in the form of pharmaceutical preparations for enteral, parenteral or topical administration. They can be administered, for example, perorally, e.g. in the form of tablets, coated tablets, dragees, hard and soft gelatine capsules, solutions, emulsions or suspensions, rectally, e.g. in the form of suppositories, parenterally, e.g. in the form of injection solutions or suspensions or infusion solutions, or topically, e.g. in the form of ointments, creams or oils. Oral administration is preferred.

The production of the pharmaceutical preparations can be effected in a manner which will be familiar to any person skilled in the art by bringing the described compounds of formula I and/or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragees and hard gelatine capsules. Suitable carrier materials for soft gelatine capsules are, for example, vegetable oils, waxes, fats and semi-solid and liquid polyols (depending on the nature of the active ingredient no carriers might, however, be required in the case of soft gelatine capsules). Suitable carrier materials for the production of solutions and syrups are, for example, water, polyols, sucrose, invert sugar. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavour-improving agents, salts for varying the osmotic pressure, buffer substances, solubilizers, colorants and masking agents and antioxidants come into consideration as pharmaceutical adjuvants.

The dosage of the compounds of formula (I) can vary within wide limits depending on the disease to be controlled, the age and the individual condition of the patient and the mode of administration, and will, of course, be fitted to the individual requirements in each particular case. For adult patients a daily dosage of about 1 to 1000 mg, especially about 1 to 300 mg, comes into consideration. Depending on severity of the disease and the precise pharmacokinetic profile the compound could be administered with one or several daily dosage units, e.g. in 1 to 3 dosage units.

The pharmaceutical preparations conveniently contain about 1-500 mg, preferably 1-100 mg, of a compound of formula (I).

The following Examples serve to illustrate the present invention in more detail. They are, however, not intended to limit its scope in any manner.

EXAMPLES

Example A

Factor Xa activity was measured spectrophotometrically in microtiter plates in a final volume of 150 µl using the following conditions: Inhibition of human factor Xa (Enzyme Research Laboratories) was tested at an enzyme concentration of 3 nM using the chromogenic substrate S-2222 (Chromogenix AB, Mölndal, Sweden) at 200 nM. The reaction kinetics of the enzyme and the substrate were linear with both time and the enzyme concentration. The inhibitors were dissolved in DMSO and tested at various concentrations up to 100 µM. The inhibitors were diluted using HNPT buffer consisting of HEPES 100 mM, NaCl 140 mM, PEG 6000 0.1% and Tween 80 0.02%, pH 7.8. The cleavage of S-2222 by human factor Xa was followed at 405 nm for 5 minutes at room temperature. The velocity of the reaction was determined by the autoreader from the slope of the linear regression fit to 7 time points (1 minute). The initial velocity for each inhibitor concentration was determined by the slope of at least 4 time points in the linear phase by a linear regression fit (mOD/min$^2$). Apparent dissociation constants $K_i$ were calculated according to Cheng and Prusoff [Cheng, Y. C.; Prusoff, W. H. Relationship between the inhibition constant ($K_i$) and the concentration of the inhibitor that causes 50 percent inhibition ($IC_{50}$) of an enzyme reaction. Biochem. Pharmacol. 1973, 22, 3099-3108.] based on the $IC_{50}$ and the respective $K_m$, determined previously ($K_i=IC_{50}/(1+S/K_m)$). The $K_m$ for the substrate used was determined under the conditions of the test with at least 5 substrate concentrations ranging from 0.5 to 15 times $K_m$. [Lottenberg R, Hall J A, Blinder M, Binder E P, Jackson C M., The action of thrombin on peptide p-nitroanilide substrates. Substrate selectivity and examination of hydrolysis under different reaction conditions. Biochim Biophys Acta. 1983 Feb. 15; 742(3):539-57]. According to Eadie [Eadie G.S. The inhibition of cholinesterase by physostigmine and prostigmine. J. Biol. Chem. 1942, 146, 85-93.], the $K_m$ for S-2222 amounted to 613 µM.

The activity of the low molecular weight substances can, moreover, be characterized in the "prothrombin time" (PT) clotting test. The substances are prepared as a 10 mM solution in DMSO and thereafter made up to the desired dilution in the same solvent. Thereafter, 0.25 ml of human plasma (obtained from whole blood anticoagulated with 1/10 volume of 108 mM Na citrate) was placed in the instrument-specific sample container. In each case 5 µl of each dilution of the substance-dilution series was then mixed with the plasma provided. This plasma/inhibitor mixture was incubated at 37° C. for 2 minutes. Thereafter, there were pipetted to the semi-automatic device (ACL, Automated Coagulation Laboratory (Instrument Laboratory)) 50 µl of plasma/inhibitor mixture in the measurement container. The clotting reaction was initiated by the addition of 0.1 ml of Dade® Innovin® (recombinant human tissue factor combined with calcium buffer and synthetic phospholipids, Dade Behring, Inc., Cat. B4212-50). The time up to the fibrin cross-linking was determined photooptically from the ACL. The inhibitor concentration, which brought about a doubling of the PT clotting time, was determined by fitting the data to an exponential regression (XLfit).

The compounds of the present invention can furthermore be characterised by the Activated Partial Thromboplastin time (aPTT). This coagulation test can e.g. be run on the ACL 300 Coagulation System (Instrumentation Laboratory) automatic analyzer. The substances are prepared as a 10 mM solution in DMSO and thereafter made up to the desired dilution in the same solvent. The test is performed with the Dade® Actin® FS Activated PTT reagent (purified soy phosphatides in $1.0 \times 10^{-4}$M ellagic acid, stabilizers and preservative, Dade Behring, Inc., Cat. B4218-100). Thereafter, 0.25 ml aliquots of human plasma (obtained from whole blood anticoagulated with 1/10 volume of 108 mM Na citrate) are spiked with 5 µl of test compound in at least 6 concentrations. 50 µl plasma at 4° C. containing 1/50 vol. inhibitor in solvent are incubated with 50 µl Dade® Actine® FS Activated PTT reagent in water at 37° C. for 3 min., then 50 µl $CaCl_2.2H_2O$ 25 mM in water at 37° C. are added. The time up to the fibrin cross-linking was determined photooptically from the ACL. The inhibitor concentration, which brought about a doubling of the APTT clotting time, was determined by fitting the data to an exponential regression (XLfit).

The $K_i$ values of the active compounds of the present invention preferably amount to about 0.001 to 50 µM, especially about 0.001 to 1 µM. The PT values preferably amount to about 0.5 to 100 µM, especially to about 0.5 to 10 µM. The aPTT values preferably amount to about 0.5 to 100 µM, especially to about 0.5 to 10 µM.

| Example | $K_i$ [nM] factor Xa |
|---|---|
| Example 3 | 19 |
| Example 16 | 51 |
| Example 18 | 12 |

Example 1

(R)-1-Methyl-4,6-dihydro-1H-pyrrolo[3,4-c]pyrazole-4,5-dicarboxylic acid 5-[(4-chloro-phenyl)-amide]-4-{[2-fluoro-4-(2-oxo-2H-pyridin-1-yl)-phenyl]-amide}

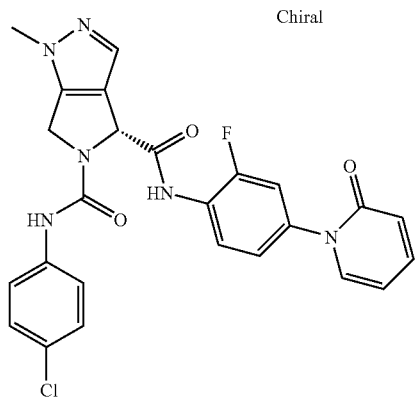

A (R)-4-[2-Fluoro-4-(2-oxo-2H-pyridin-1-yl)-phenylcarbamoyl]-1-methyl-4,6-dihydro-1H-pyrrolo[3,4-c]pyrazole-5-carboxylic acid tert-butyl ester To a solution of (R)-1-methyl-4,6-dihydro-1H-pyrrolo[3,4-c]pyrazole-4,5-dicarboxylic acid 5-tert-butyl ester (478 mg, described in US2002/0193399), 1-(4-amino-3-fluoro-phenyl)-1H-pyridin-2-one (365 mg; CAS 536747-52-1) and DIPEA (0.46 ml) in 20 ml acetonitrile and 2 ml DMF was added BOPCl (1.366 g). The reaction mixture was stirred for 24 h at rt, diluted with AcOEt and washed with 1M HCl, 1M NaOH and brine. The organic layers were dried over magnesium sulfate, evaporated and purified by chromatography (silica gel; AcOEt) to deliver the title compound as a yellow oil (510 mg). MS: 454.5 (M+H)+

B (R)-1-Methyl-1,4,5,6-tetrahydro-pyrrolo[3,4-c] pyrazole-4-carboxylic acid [2-fluoro-4-(2-oxo-2H-pyridin-1-yl)-phenyl]-amide A solution of (R)-4-[2-fluoro-4-(2-oxo-2H-pyridin-1-yl)-phenylcarbamoyl]-1-methyl-4,6-dihydro-1H-pyrrolo[3,4-c]pyrazole-5-carboxylic acid tert-butyl ester (258 mg) in 1 ml 4M HCl/dioxane was stirred 18 h at rt. The reaction mixture was portionned between AcOEt and 1M NaOH/ice. The organic layers were washed with brine, dried over magnesium sulfate and evaporated to deliver a white residue (115 mg) of the title compound. MS: 354.3 (M+H)+

C(R)-1-Methyl-4,6-dihydro-1H-pyrrolo[3,4-c]pyrazole-4,5-dicarboxylic acid 5-[(4-chloro-phenyl)-amide]4-{[2-fluoro-4-(2-oxo-2H-pyridin-1-yl)-phenyl]-amide}

To a solution of (R)-1-methyl-1,4,5,6-tetrahydro-pyrrolo [3,4-c]pyrazole-4-carboxylic acid [2-fluoro-4-(2-oxo-2H-pyridin-1-yl)-phenyl]-amide (83 mg) in 2 ml dichloromethane at 0° C., 4-chlorophenyl-isocyanate (72 mg) was added. The reaction mixture was kept for 2 hrs under ice cooling, then heptane was added and the precipitate filtrated. (R)-1-Methyl-4,6-dihydro-1H-pyrrolo[3,4-c]pyrazole-4,5- dicarboxylic acid 5-[(4-chloro-phenyl)-amide]4-{[2-fluoro-4-(2-oxo-2H-pyridin-1-yl)-phenyl]-amide} was obtained as a white solid (119 mg). MS: 507.2 (M+H)+

Example 2

(R) 1-Methyl-4,6-dihydro-1H-pyrrolo[3,4-c]pyrazole-4,5-dicarboxylic acid 4-{[2-fluoro-4-(2-oxo-2H-pyridin-1-yl)-phenyl]-amide}5-[(4-methoxyphenyl)-amide]

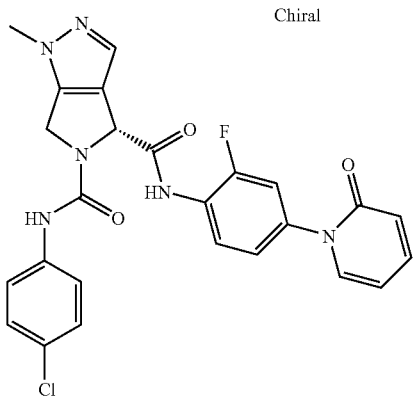

Using the same procedure described in example 1 and 4-methoxyphenyl-isocyanate as reagent in the last step, the title compound was delivered as a white solid (29 mg). MS: 503.1 (M+H)+

Example 3

(R)-1-Methyl-4,6-dihydro-1H-pyrrolo[3,4-c]pyrazole-4,5-dicarboxylic acid 5-[(5-chloro-pyridin-2-yl)-amide]4-{[2-fluoro-4-(2-oxo-2H-pyridin-1-yl)-phenyl]-amide}

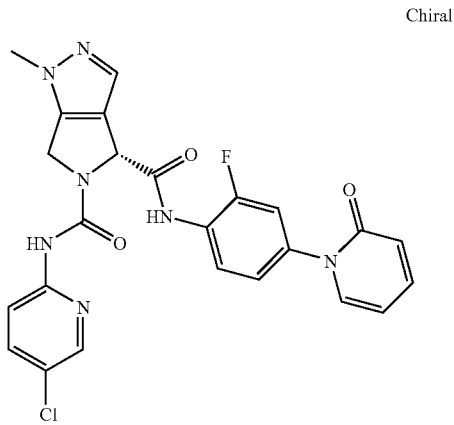

A solution of (R)-1-Methyl-1,4,5,6-tetrahydro-pyrrolo[3,4-c]pyrazole-4-carboxylic acid [2-fluoro-4-(2-oxo-2H-pyridin-1-yl)-phenyl]-amide (example 1B, 36 mg), (5-chloro-pyridin-2-yl)-carbamic acid 4-nitro-phenyl ester (44 mg; CAS 536746-34-6) and DIPEA (0.042 ml) in 2 ml DMF was heated for 4 hrs at 90° C. The reaction mixture was cooled, diluted with AcOEt, washed twofold with 1M NaOH, 1M HCl and brine. The aqueous layers were extracted with AcOEt, dried over magnesium sulfate, evaporated and purified by chromatography (silica gel, AcOEt) to yield the title compound as a white solid (8 mg). MS: 508.3 (M+H)+

Example 4

(R)-5-(1H-Indole-6-carbonyl)-1-methyl-1,4,5,6-tetrahydro-pyrrolo[3,4-c]pyrazole-4-carboxylic acid [2-fluoro-4-(2-oxo-2H-pyridin-1-yl)-phenyl]-amide

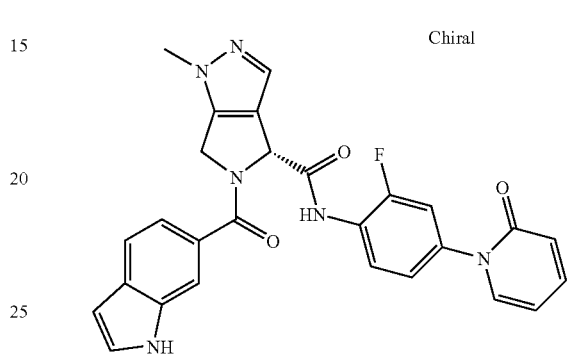

A solution of (R)-1-methyl-1,4,5,6-tetrahydro-pyrrolo[3,4-c]pyrazole-4-carboxylic acid [2-fluoro-4-(2-oxo-2H-pyridin-1-yl)-phenyl]-amide (example 1B, 38 mg), 6-indolecarboxylic acid (22 mg), 0.03 ml (DIPEA) and BOPCl (51 mg) in 2 ml acetonitrile was stirred for 2 hrs at 0° C. A consecutive basic and acidic work up delivered a yellow oil which was purified by chromatography (silica gel, AcOEt). (R)-5-(1H-Indole-6-carbonyl)-1-methyl-1,4,5,6-tetrahydro-pyrrolo[3,4-c]pyrazole-4-carboxylic acid [2-fluoro-4-(2-oxo-2H-pyridin-1-yl)-phenyl]-amide was obtained as a white solid (13 mg). MS: 497.0 (M+H)+

Example 5

(S)-1-Methyl-4,6-dihydro-1H-pyrrolo[3,4-c]pyrazole-4,5-dicarboxylic acid 5-[(4-chloro-phenyl)-amide]4-{[2-fluoro-4-(2-oxo-2H-pyridin-1-yl)-phenyl]-amide}

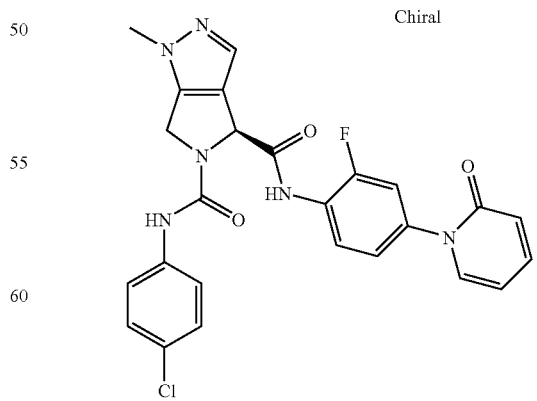

Using the same procedure described in example 1, but starting from (S)-1-methyl-4,6-dihydro-1H-pyrrolo[3,4-c]

pyrazole-4,5-dicarboxylic acid 5-tert-butyl ester, the title compound was obtained as a white solid (14 mg). MS: 507.2 (M+H)+

Example 6

1-Methyl-4,6-dihydro-1H-pyrrolo[3,4-c]pyrazole-4,5-dicarboxylic acid 5-[(4-chloro-phenyl)-amide]4-{[4-(2-oxo-2H-pyrazin-1-yl)-phenyl]-amide}

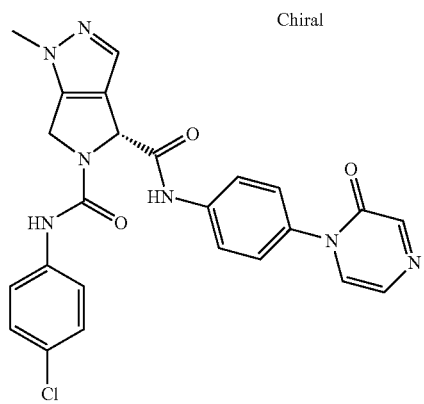

Using the same procedure described in example 1 (with 1-(4-amino-phenyl)-1H-pyrazin-2-one, CAS 4444002-64-6) the title compound was obtained as a white solid (35 mg). MS: 490.8 (M+H)+

Example 7

1-Methyl-4,6-dihydro-1H-pyrrolo[3,4-c]pyrazole-4,5-dicarboxylic acid 5-[(4-chloro-phenyl)-amide]4-{[2-fluoro-4-(2-oxo-2H-pyrazin-1-yl)-phenyl]-amide}

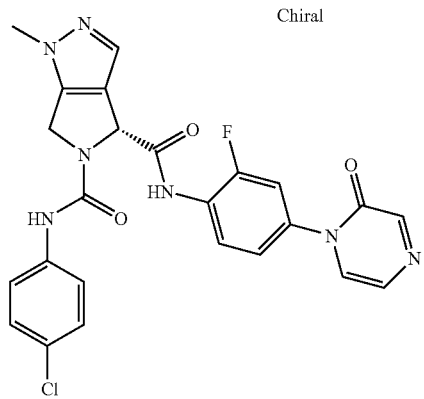

Using the same procedure described in example 1 using 1-(4-amino-3-fluoro-phenyl)-1H-pyrazin-2-one (prepared from 2-fluoro-4-iodoaniline by reaction with 1H-pyrazin-2-one, Cu(I)I, N,N'-dimethylethylenediamine and cesium carbonate in dioxane at 120° C.), the title compound was obtained as a white solid (15 mg). MS: 508.0 (M+H)+

Example 8

(R)-1-Methyl-4,6-dihydro-1H-pyrrolo[3,4-c]pyrazole-4,5-dicarboxylic acid 5-[(4-chloro-phenyl)-amide]4-{[2-fluoro-4-(3-oxo-morpholin-4-yl)-phenyl]-amide}

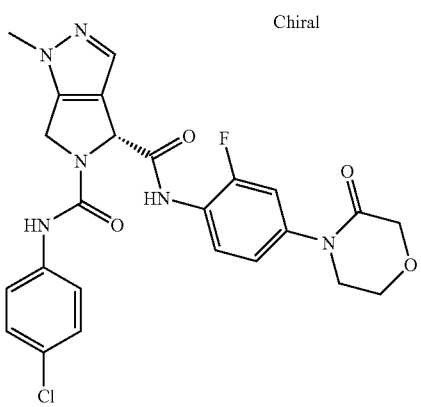

Using the same procedure described in example 1 (with 4-(4-amino-3-fluoro-phenyl)-morpholin-3-one, CAS 742073-22-9) the title compound was obtained as a white solid (88 mg). MS: 513.3 (M+H)+

Example 9

(R)-1-Methyl-4,6-dihydro-1H-pyrrolo[3,4-c]pyrazole-4,5-dicarboxylic acid 5-[(4-chloro-phenyl)-amide]4-{[4-(2-oxo-2H-pyridin-1-yl)-phenyl]-amide}

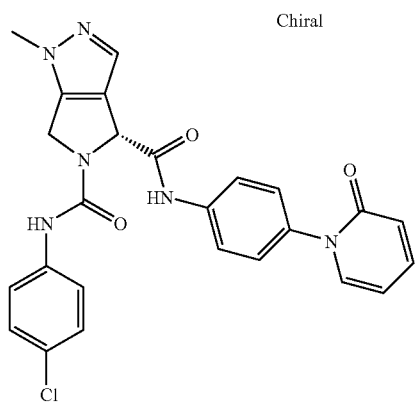

Using the same procedure described in example 1 (with 1-(4-amino-phenyl)-1H-pyridin-2-one, CAS 13143-47-0) the title compound was obtained as a white solid (25 mg). MS: 489.1 (M+H)+

Example 10

(R)-1-Methyl-4,6-dihydro-1H-pyrrolo[3,4-c]pyrazole-4,5-dicarboxylic acid 5-[(3-fluoro-4-methoxyphenyl)-amide]4-{[2-fluoro-4-(2-oxo-2H-pyridin-1-yl)-phenyl]-amide}

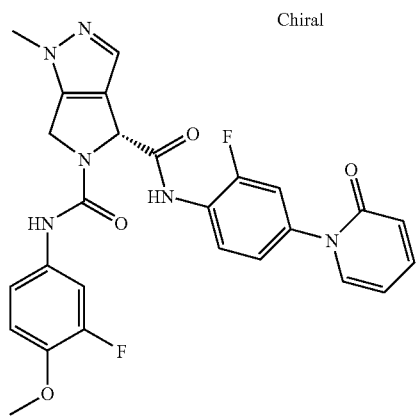

Using the same procedure described in example 3 and (3-fluoro-4-methoxy-phenyl)-carbamic acid 4-nitro-phenyl ester (prepared from 3-fluoro-4-methoxy-aniline by reaction with p-nitrophenyl chloroformat and pyridine in dichloromethane) the title compound was obtained as a white solid (26 mg). MS: 521.2 (M+H)+

Example 11

(R)-1-Methyl-4,6-dihydro-1H-pyrrolo[3,4-c]pyrazole-4,5-dicarboxylic acid 5-[(4-chloro-phenyl)-amide]5-{[2,6-difluoro-4-(2-oxo-2H-pyridin-1-yl)-phenyl]-amide}

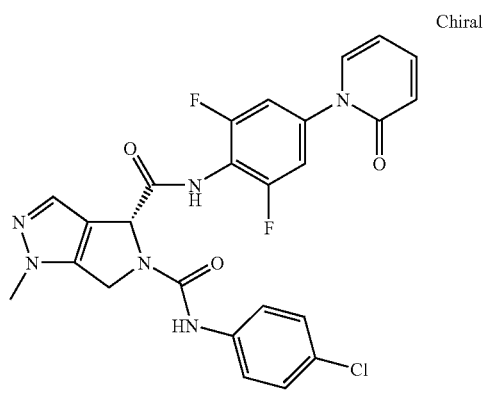

Using the same procedure described in example 1 (with 1-(4-amino-3,5-difluoro-phenyl)-1H-pyridin-2-one prepared from 4-bromo-2,6-difluoroaniline by reaction with 2-hydroxypyridine, Cu(I)I, potassium carbonate, 8-hydroxyquinoline in DMSO at 150° C.) the title compound was obtained as a white solid (110 mg). MS: 525.3 (M+H)+

Example 12

(R)-1-Methyl-4,6-dihydro-1H-pyrrolo[3,4-c]pyrazole-4,5-dicarboxylic acid 5-[(5-chloro-pyridin-2-yl)-amide]4-{[2-fluoro-4-(2-oxo-2H-pyrazin-1-yl)-phenyl]-amide}

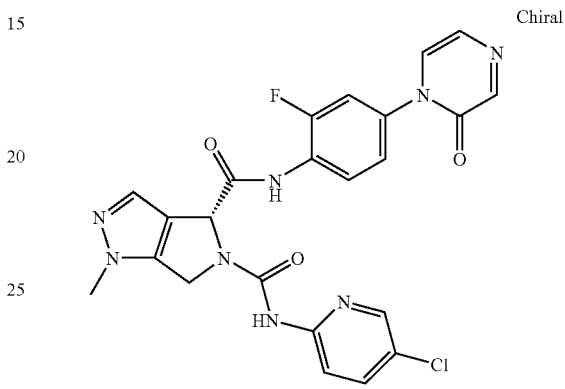

Using the same procedure described in example 1 (with 1-(4-amino-3-fluoro-phenyl)-1H-pyrazin-2-one) and for the last step following the method described in example 3, the title compound was obtained as a white solid (70 mg). MS: 509.5 (M+H)+

Example 13

(R)-1-Methyl-4,6-dihydro-1H-pyrrolo[3,4-c]pyrazole-4,5-dicarboxylic acid 4-{[2-fluoro-4-(3-oxo-morpholin-4-yl)-phenyl]-amide}5-[(4-methoxy-phenyl)-amide]

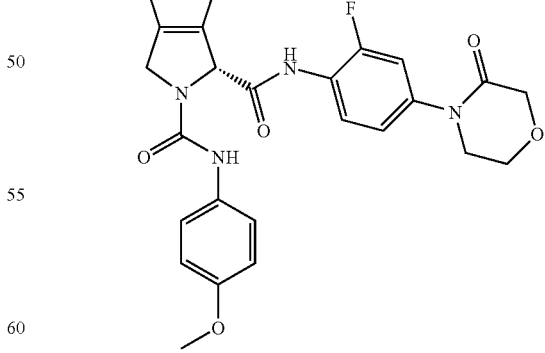

Using the same procedure described in example 1 (with 4-(4-amino-3-fluoro-phenyl)-morpholin-3-one, CAS 742073-22-9) and using 4-methoxyphenyl-isocyanate in the last step, the title compound was obtained as a white solid (33 mg). MS: 507.4 (M−H)−

Example 14

(R)-1-Methyl-4,6-dihydro-1H-pyrrolo[3,4-c]pyrazole-4,5-dicarboxylic acid 5-[(5-chloro-pyridin-2-yl)-amide]4-{[2-fluoro-4-(3-oxo-morpholin-4-yl)-phenyl]-amide}

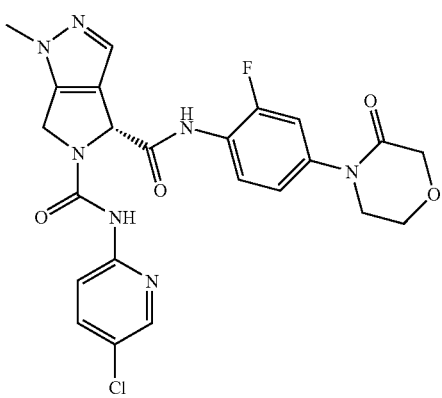

Using the same procedure described in example 1 (with 4-(4-amino-3-fluoro-phenyl)-morpholin-3-one, CAS 742073-22-9) and in the last step the procedure described in example 3, the title compound was obtained as a white solid (27 mg). MS: 514.2 (M+H)+

Example 15

(R)-1-Methyl-4,6-dihydro-1H-pyrrolo[3,4-c]pyrazole-4,5-dicarboxylic acid 5-[(3-fluoro-4-methoxy-phenyl)-amide]4-{[2-fluoro-4-(3-oxo-morpholin-4-yl)-phenyl]-amide}

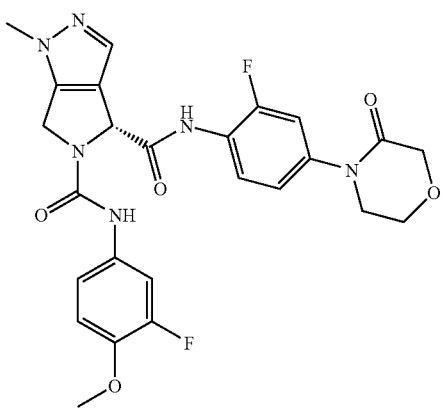

Using the same procedure described in example 1 (with 4-(4-amino-3-fluoro-phenyl)-morpholin-3-one, CAS 742073-22-9) and in the last step the procedure described in example 3 using (3-fluoro-4-methoxy-phenyl)-carbamic acid 4-nitro-phenyl ester (prepared from 3-fluoro-4-methoxy-aniline by reaction with p-nitrophenyl chloroformat and pyridine in dichloromethane) the title compound was obtained as a white solid (26 mg). MS: 523.1 (M+H)+

Example 16

2,3-Dihydro-pyrrolo[2,3-b]pyridine-1,2-dicarboxylic acid 1-[(4-chloro-phenyl)-amide]2-{[2-fluoro-4-(2-oxo-2H-pyridin-1-yl)-phenyl]-amide}

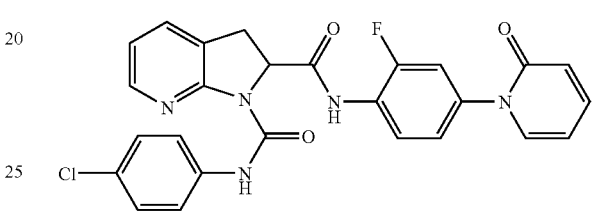

A 2,3-Dihydro-pyrrolo[2,3-b]pyridine-1,2-dicarboxylic acid 1-tert-butyl ester 2-ethyl ester A solution of pyrrolo[2,3-b]pyridine-1,2-dicarboxylic acid 1-tert-butyl ester 2-ethyl ester (9.53 g; CAS 577711-88-7) in 240 ml ethanol was treated with 5% Pd/C2 h at 40° C. under a hydrogene atmosphere. The reaction mixture was filtered and the title compound obtained as a yellow oil (9.3 g).

B 2,3-Dihydro-pyrrolo[2,3-b]pyridine-1,2-dicarboxylic acid 1-tert-butyl ester A suspension of 2,3-dihydro-pyrrolo[2,3-b]pyridine-1,2-dicarboxylic acid 1-tert-butyl ester 2-ethyl ester (1 g) and lithium hydroxide (0.25 g) in 6 ml THF, 3 ml MeOH and 3 ml water was stirred 0.5 h at rt. The reaction mixture was poured onto 1M HCl/ice and washed three times with dichloromethane. The aqueous layer was neutralized with 1M NaOH, evaporated to dryness and purified by chromatography (silica gel, dichloromethane/methanol, 4/1) to yield 2,3-dihydro-pyrrolo[2,3-b]pyridine-1,2-dicarboxylic acid 1-tert-butyl ester as a white solid (400 mg). MS: 263.4 (M–H)−

C 2,3-Dihydro-pyrrolo[2,3-b]pyridine-1,2-dicarboxylic acid 1-[(4-chloro-phenyl)-amide]2-{[2-fluoro-4-(2-oxo-2H-pyridin-1-yl)-phenyl]-amide}

Starting from 2,3-dihydro-pyrrolo[2,3-b]pyridine-1,2-dicarboxylic acid 1-tert-butyl ester and using the procedure described in example 1,2,3-dihydro-pyrrolo[2,3-b]pyridine-1,2-dicarboxylic acid 1-[(4-chloro-phenyl)-amide]2-{[2-fluoro-4-(2-oxo-2H-pyridin-1-yl)-phenyl]-amide}was obtained as a white solid (63 mg). MS: 504.3 (M+H)+

Example 17

2,3-Dihydro-pyrrolo[2,3-b]pyridine-1,2-dicarboxylic acid 1-[(5-chloro-pyridin-2-yl)-amide]2-{[2-fluoro-4-(2-oxo-2H-pyridin-1-yl)-phenyl]-amide}

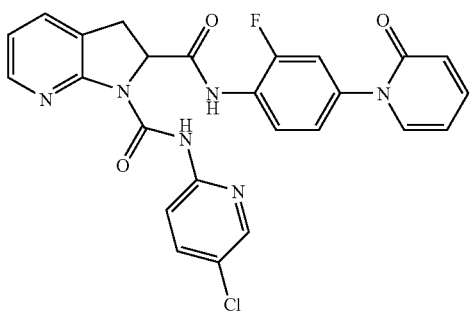

Starting from 2,3-dihydro-pyrrolo[2,3-b]pyridine-1,2-dicarboxylic acid 1-tert-butyl ester and using the procedure described in example 3, the title compound was obtained as a white solid (20 mg). MS: 505.2 (M+H)+

Example 18

5,8-Dihydro-6H-[1,7]naphthyridine-6,7-dicarboxylic acid 7-[(4-chloro-phenyl)-amide]6-{[2-fluoro-4-(2-oxo-2H-pyridin-1-yl)-phenyl]-amide}

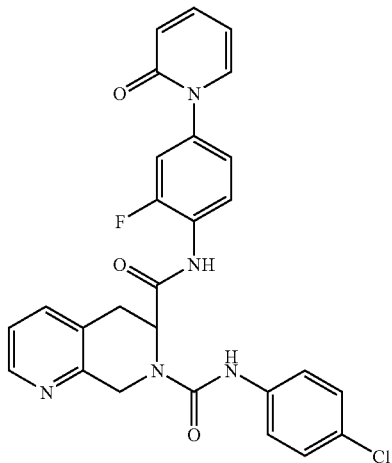

A 5,8-Dihydro-6H-[1,7]naphthyridine-6,7-dicarboxylic acid 7-tert-butyl ester and 7,8-Dihydro-5H-[1,6]naphthyridine-6,7-dicarboxylic acid 6-tert-butyl ester To a solution of 5,6,7,8-tetrahydro-[1,7]naphthyridine-6-carboxylic acid methyl ester hydrochloride and 5,6,7,8-tetrahydro-[1,6]naphthyridine-7-carboxylic acid methyl ester hydrochloride (500 mg)) in 12 ml acetonitrile and 1 ml water under ice cooling, were added successively Boc2O (478 mg), triethylamine (1.11 ml) and DMAP (12 mg). The reaction mixture was stirred 2 h at rt, evaporated and purified by chromatography (silica gel, dichloromethane/methanol, 4/1) to yield a mixture of the two compounds as a yellow residue (313 mg). MS: 277.4 (M−H)−

B 7-[2-Fluoro-4-(2-oxo-2H-pyridin-1-yl)-phenylcarbamoyl]-7,8-dihydro-5H-[1,6]naphthy-ridine-6-carboxylic acid tert-butyl ester and 6-[2-fluoro-4-(2-oxo-2H-pyridin-1-yl)-phenylcarbamoyl]-5,8-dihydro-6H-[1,7]naphthyridine-7-carboxylic acid tert-butyl ester To a solution of the above mixture (707 mg) in 20 ml THF was added lithium hydroxide (58 mg) and vigorously stirred for 15 min. Then, molecular sieves was added, followed by N-methylmorpholine (0.84 ml). The reaction mixture was cooled, treated with isobutyl chloroformate (0.49 ml) and stirred for 30 min. After addition of 1-(4-amino-3-fluorophenyl)-1H-pyridin-2-one (622 mg; CAS 536747-52-1), the suspension was kept for 1 h at 0° C. and for 18 hrs at rt. The reaction mixture was evaporated and filtrated. The residue was diluted with dichloromethane and washed with water and brine. The organic layers were dried over magnesium sulfate, evaporated and purified by chromatography (silica gel, AcOEt/MeOH, 50:1) to deliver the two isomers. 6-[2-Fluoro-4-(2-oxo-2H-pyridin-1-yl)-phenylcarbamoyl]-5,8-dihydro-6H-[1,7]naphthyridine-7-carboxylic acid tert-butyl ester was obtained as a white solid (205 mg; Rf=0.5, AcOEt/MeOH 19:1) and 7-[2-fluoro-4-(2-oxo-2H-pyridin-1-yl)-phenylcarbamoyl]-7,8-dihydro-5H-[1,6]naph-thyridine-6-carboxylic acid tert-butyl ester as a light yellow solid (351 mg; Rf=0.4, AcOEt/MeOH 19:1). MS: 465.5 (M+H)+

C 5,6,7,8-Tetrahydro-[1,7]naphthyridine-6-carboxylic acid[2-fluoro-4-(2-oxo-2H-pyridin-1-yl)-phenyl]-amide A solution of 7-[2-fluoro-4-(2-oxo-2H-pyridin-1-yl)-phenylcarbamoyl]-7,8-dihydro-5H-[1,6]naphthyridine-6-carboxylic acid tert-butyl ester (310 mg) in 8 ml dichloromethane and 1.53 ml TFA was stirred for 4 hrs at rt. The reaction mixture was poured onto 1M NaOH/ice and extracted twice with dichloromethane. The organic layers were dried over magnesium sulfate, evaporated and purified by chromatography (silica gel, AcOEt/methanol 9:1) to deliver the title compound as a light yellow solid (151 mg). MS: 365.5 (M+H)+

D 5,8-Dihydro-6H-[1,7]naphthyridine-6,7-dicarboxylic acid 7-[(4-chloro-phenyl)-amide]6-{[2-fluoro-4-(2-oxo-2H-pyridin-1-yl)-phenyl]-amide}

To a solution of 5,6,7,8-tetrahydro-[1,7]naphthyridine-6-carboxylic acid[2-fluoro-4-(2-oxo-2H-pyridin-1-yl)-phenyl]-amide (40 mg) in 4 ml THF at −78° C., was added a solution of 4-chlorophenylisocyannate in 2 ml THF. After 30 nm, the reaction mixture was kept at rt for 1 h, diluted with heptane and the white precipitate of the title compound was filtered (38 mg). MS: 518.5 (M+H)+

Example 19

7,8-Dihydro-5H-[1,6]naphthyridine-6,7-dicarboxylic acid 6-[(4-chloro-phenyl)-amide]7-{[2-fluoro-4-(2-oxo-2H-pyridin-1-yl)-phenyl]-amide}

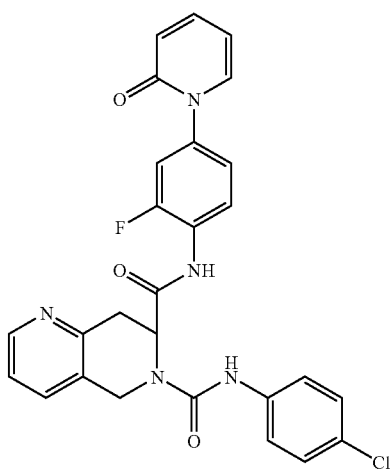

A 5,6,7,8-Tetrahydro-[1,6]naphthyridine-7-carboxylic acid[2-fluoro-4-(2-oxo-2H-pyridin-1-yl)-phenyl]-amide A solution of 6-[2-fluoro-4-(2-oxo-2H-pyridin-1-yl)-phenylcarbamoyl]-5,8-dihydro-6H-[1,7]naphthyridine-7-carboxylic acid tert-butyl ester (170 mg; example 16B) in 5 ml dichloromethane and 0.84 ml TFA was stirred for 4 hrs at rt. The reaction mixture was poured onto 1M NaOH/ice and extracted twice with dichloromethane. The organic layers were dried over magnesium sulfate and evaporated to deliver the title compound as a white foam (123 mg). MS: 365.5 (M+H)$^+$

B 7,8-Dihydro-5H-[1,6]naphthyridine-6,7-dicarboxylic acid 6-[(4-chloro-phenyl)-amide]7-{[2-fluoro-4-(2-oxo-2H-pyridin-1-yl)-phenyl]-amide}

This compound prepared from 5,6,7,8-tetrahydro-[1,6]naphthyridine-7-carboxylic acid [2-fluoro-4-(2-oxo-2H-pyridin-1-yl)-phenyl]-amide with the procedure described in example 16D) was obtained as a white solid (50 mg). MS: 518.5 (M+H)$^+$

Example A

Film coated tablets containing the following ingredients can be manufactured in a conventional manner:

| Ingredients | Per tablet | |
| --- | --- | --- |
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |

-continued

| Ingredients | Per tablet | |
| --- | --- | --- |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titan dioxide | 0.8 mg | 1.6 mg |

The active ingredient is sieved and mixed with microcristalline cellulose and the mixture is granulated with a solution of polyvinylpyrrolidon in water. The granulate is mixed with sodium starch glycolate and magesiumstearate and compressed to yield kernels of 120 or 350 mg respectively. The kernels are lacquered with an aqueous solution/suspension of the above mentioned film coat.

Example B

Capsules containing the following ingredients can be manufactured in a conventional manner:

| Ingredients | Per capsule |
| --- | --- |
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example C

Injection solutions can have the following composition:

| | |
| --- | --- |
| Compound of formula (I) | 3.0 mg |
| Polyethylene Glycol 400 | 150.0 mg |
| Acetic Acid | q.s. ad pH 5.0 |
| Water for injection solutions | ad 1.0 ml |

The active ingredient is dissolved in a mixture of Polyethylene Glycol 400 and water for injection (part). The pH is adjusted to 5.0 by Acetic Acid. The volume is adjusted to 1.0 ml by addition of the residual amount of water. The solution is filtered, filled into vials using an appropriate overage and sterilized.

Example D

Soft gelatin capsules containing the following ingredients can be manufactured in a conventional manner:

| Capsule contents | |
| --- | --- |
| Compound of formula (I) | 5.0 mg |
| Yellow wax | 8.0 mg |
| Hydrogenated Soya bean oil | 8.0 mg |
| Partially hydrogenated plant oils | 34.0 mg |

-continued

| | |
|---|---|
| Soya bean oil | 110.0 mg |
| Weight of capsule contents | 165.0 mg |
| Gelatin capsule | |
| Gelatin | 75.0 mg |
| Glycerol 85% | 32.0 mg |
| Karion 83 | 8.0 mg (dry matter) |
| Titan dioxide | 0.4 mg |
| Iron oxide yellow | 1.1 mg |

The active ingredient is dissolved in a warm melting of the other ingredients and the mixture is filled into soft gelatin capsules of appropriate size. The filled soft gelatin capsules are treated according to the usual procedures.

Example E

Sachets containing the following ingredients can be manufactured in a conventional manner:

| | |
|---|---|
| Compound of formula (I) | 50.0 mg |
| Lactose, fine powder | 1015.0 mg |
| Microcristalline cellulose (AVICEL PH 102) | 1400.0 mg |
| Sodium carboxymethyl cellulose | 14.0 mg |
| Polyvinylpyrrolidon K 30 | 10.0 mg |
| Magnesiumstearate | 10.0 mg |
| Flavoring additives | 1.0 mg |

The active ingredient is mixed with lactose, microcristalline cellulose and sodium carboxymethyl cellulose and granulated with a mixture of polyvinylpyrrolidon in water. The granulate is mixed with magnesiumstearate and the flavouring additives and filled into sachets.

The invention claimed is:

1. A compound of formula 1d:

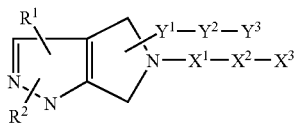

(Id)

or pharmaceutically acceptable salt thereof wherein:
$R^1$ and $R^2$ are independently selected from the group consisting of:
(1) hydrogen,
(2) $C_{1-6}$ alkyl,
(3) $C_{1-6}$ alkoxy,
(4) fluoro $C_{1-6}$ alkoxy,
(5) hydroxy $C_{1-6}$ alkoxy,
(6) $C_{1-6}$ alkoxy $C_{1-6}$ alkoxy,
(7) mono or di $C_{1-6}$ alkyl substituted amino $C_{1-6}$ alkoxy,
(8) halogen,
(9) cyano,
(10) nitro,
(11) —N(R')—CO—($C_{1-6}$ alkyl optionally substituted by one or more fluorine atoms) wherein R' is hydrogen, $C_{1-6}$ alkyl or fluoro $C_{1-6}$ alkyl,
(12) —N(R')—CO—O—($C_{1-6}$ alkyl optionally substituted by one or more fluorine atoms) wherein R' is hydrogen, $C_{1-6}$ alkyl or fluoro $C_{1-6}$ alkyl,
(13) —N(R')—CO—N(R'')(R''') wherein R', R'' and R''' are independently hydrogen, $C_{1-6}$ alkyl or fluoro $C_{1-6}$ alkyl,
(14) —N(R')—SO$_2$—($C_{1-6}$ alkyl optionally substituted by one or more fluorine atoms) wherein R' is hydrogen, $C_{1-6}$ alkyl or fluoro $C_{1-6}$ alkyl; and
(15) —SO$_2$—N(R')(R''), —C(O)—N(R')(R'') or —N(R')(R'') wherein R' and R'' are independently selected from the group consisting of hydrogen, $C_{1-6}$ alkyl and fluoro $C_{1-6}$ alkyl, or alternatively, R' and R'', together with the nitrogen atom to which they are attached, form a heterocycyl;
$X^1$ is —C(O)—NH— or —C(O)—;
—$X^2$—$X^3$ forms phenyl or pyridyl, wherein said phenyl or pyridyl is optionally substituted by one or more halogen atoms;
$Y^1$ is —C(O)—NH—;
$Y^2$ is 1,4-phenylene optionally substituted by one or more halogen atoms;
$Y^3$ is hydrogen, aryl, heteroaryl or heterocyclyl, wherein one or two carbon atoms of the aryl, heteroaryl or heterocyclyl may be optionally replaced with a carbonyl group and wherein the aryl, heteroaryl or heterocyclyl may be optionally substituted by one or more substituents indepenently selected from the group consisting of:
(1) $C_{1-6}$ alkyl,
(2) $C_{1-6}$ alkoxy,
(3) halogen,
(4) cyano,
(5) nitro,
(6) amino,
(7) mono-$C_{1-6}$ alkyl substituted amino,
(8) di-$C_{1-6}$ alkyl substituted amino
(9) mono-$C_{1-6}$ alkyl substituted amino-$C_{1-6}$ alkyl,
(10) di-$C_{1-6}$ alkyl substituted amino-$C_{1-6}$ alkyl,
(11) —SO$_2$—$C_{1-6}$ alkyl,
(12) —SO$_2$—NH$_2$,
(13) —SO$_2$—NH—$C_{1-6}$ alkyl and
(14) —SO$_2$—N($C_{1-6}$ alkyl)$_2$.

2. A compound according to claim 1, wherein $X^1$ is —C(O)—NH—.

3. A compound according to claim 1, wherein $X^1$ is —C(O)—.

4. A compound according to claim 1, wherein —$X^2$—$X^3$ forms phenyl, wherein said phenyl is optionally substituted by one or more halogen atoms.

5. A compound according to claim 1, wherein —$X^2$—$X^3$ forms pyridyl, wherein said pyridyl is optionally substituted by one or more halogen atoms.

6. A compound according to claim 1, wherein —$X^2$—$X^3$ forms 4-chlorophenyl or 5-chloropyridyn-2-yl.

7. A compound according to claim 1, wherein $Y^2$ is 2-fluoro-1,4 phenylene.

8. A compound according to claim 1, wherein $Y^3$ is heteroaryl optionally substituted by one or more substituents independently selected from the group consisting of $C_{1-6}$ alkyl, $C_{1-6}$ alkoxy, halogen, cyano, nitro, amino, mono-$C_{1-6}$ alkyl substituted amino, di-$C_{1-6}$ alkyl substituted amino, mono-$C_{1-6}$ alkyl substituted amino-$C_{1-6}$ alkyl, di-$C_{1-6}$ alkyl substituted amino-$C_{1-6}$ alkyl, —SO$_2$—$C_{1-6}$ alkyl, —SO$_2$—NH$_2$, —SO$_2$—NH—$C_{1-6}$ alkyl and —SO$_2$—N($C_{1-6}$ alkyl)$_2$, wherein one or two carbon atoms of said heteroaryl are optionally replaced with a carbonyl group.

9. A compound according to claim 1, wherein $Y^3$ is 2-oxo-2H-pyridyn-1-yl.

10. A compound according to claim 1, wherein one of $R^1$ and $R^2$ is hydrogen, and the other is $C_{1-6}$ alkyl.

11. A compound according to claim 1, wherein one of $R^1$ and $R^2$ is hydrogen, and the other is $C_{1-6}$ alkyl at the 1 position of the pyrrolopyrazole ring.

12. A compound according to claim 1, wherein one of $R^1$ and $R^2$ is hydrogen, and the other is methyl at the 1 position of the pyrrolopyrazole ring.

13. A compound according to claim 1, selected from the group consisting of:

(R)-1-Methyl-4,6-dihydro-1H-pyrrolo[3,4-c]pyrazole-4, 5-dicarboxylic acid 5-[(4-chloro-phenyl)-amide]4-{[2-fluoro-4-(2-oxo-2H-pyridin-1-yl)-phenyl]-amide}, (R)-1-Methyl-4,6-dihydro-1H-pyrrolo[3,4-c]pyrazole-4, 5-dicarboxylic acid 5-[(4-chloro-phenyl)-amide]4-{[4-(2-oxo-2H-pyrazin-1-yl)-phenyl]-amide}, (R)-1-Methyl-4,6-dihydro-1H-pyrrolo[3,4-c]pyrazole-4, 5-dicarboxylic acid 5-[(4-chloro-phenyl)-amide]4-{[2-fluoro-4-(2-oxo-2H-pyrazin-1-yl)-phenyl]-amide}, (R)-1-Methyl-4,6-dihydro-1H-pyrrolo[3,4-c]pyrazole-4, 5-dicarboxylic acid 5-[(4-chloro-phenyl)-amide]4-{[4-(2-oxo-2H-pyridin-1-yl)-phenyl]-amide} and (R)-1-Methyl-4,6-dihydro-1H-pyrrolo[3,4-c]pyrazole-4, 5-dicarboxylic acid 5-[(4-chloro-phenyl)-amide]4-{[2,6-difluoro-4-(2-oxo-2H-pyridin-1-yl)-phenyl]-amide}.

14. A compound according to claim 1, wherein $Y^2$ is 1,4-phenylene optionally substituted by one or more halogen atoms.

15. A pharmaceutical composition comprising a compound according to claim 1, and a pharmaceutically acceptable excipient.

16. A compound according to claim 1, selected from the group consisting of:

(R)-1-Methyl-4,6-dihydro-1H-pyrrolo[3,4-c]pyrazole-4, 5-dicarboxylic acid 5-[(4-chloro-phenyl)-amide]-4-{[2-fluoro-4-(2-oxo-2H-pyridin-1-yl)-phenyl]-amide};

(R)-1-Methyl-4,6-dihydro-1H-pyrrolo[3,4-c]pyrazole-4, 5-dicarboxylic acid 4-{[2-fluoro-4-(2-oxo-2H-pyridin-1-yl)-phenyl]-amide}5-[(4-methoxy-phenyl)-amide];

(R)-1-Methyl-4,6-dihydro-1H-pyrrolo[3,4-c]pyrazole-4, 5-dicarboxylic acid 5-[(5-chloro-pyridin-2-yl)-amide] 4-{[2-fluoro-4-(2-oxo-2H-pyridin-1-yl)-phenyl]-amide};

and any pharmaceutically acceptable salt thereof.

17. A compound according to claim 1, selected from the group consisting of:

(R)-5-(1H-Indole-6-carbonyl)-1-methyl-1,4,5,6-tetrahydro-pyrrolo[3,4-c]pyrazole-4-carboxylic acid [2-fluoro-4-(2-oxo-2H-pyridin-1-yl)-phenyl]-amide;

(S)-1-Methyl-4,6-dihydro-1H-pyrrolo[3,4-c]pyrazole-4, 5-dicarboxylic acid 5-[(4-chloro-phenyl)-amide]4-{[2-fluoro-4-(2-oxo-2H-pyridin-1-yl)-phenyl]-amide};

1-Methyl-4,6-dihydro-1H-pyrrolo[3,4-c]pyrazole-4,5-dicarboxylic acid 5-[(4-chloro-phenyl)-amide]4-{[4-(2-oxo-2H-pyrazin-1-yl)-phenyl]-amide};

and any pharmaceutically acceptable salt thereof.

18. A compound according to claim 1, selected from the group consisting of:

1-Methyl-4,6-dihydro-1H-pyrrolo[3,4-c]pyrazole-4,5-dicarboxylic acid 5-[(4-chloro-phenyl)-amide]4-{[2-fluoro-4-(2-oxo-2H-pyrazin-1-yl)-phenyl]-amide};

(R)-1-Methyl-4,6-dihydro-1H-pyrrolo[3,4-c]pyrazole-4, 5-dicarboxylic acid 5-[(4-chloro-phenyl)-amide]4-{[2-fluoro-4-(3-oxo-morpholin-4-yl)-phenyl]-amide};

(R)-1-Methyl-4,6-dihydro-1H-pyrrolo[3,4-c]pyrazole-4, 5-dicarboxylic acid 5-[(4-chloro-phenyl)-amide]4-{[4-(2-oxo-2H-pyridin-1-yl)-phenyl]-amide};

and any pharmaceutically acceptable salt thereof.

19. A compound according to claim 1, selected from the group consisting of:

(R)-1-Methyl-4,6-dihydro-1H-pyrrolo[3,4-c]pyrazole-4, 5-dicarboxylic acid 5-[(3-fluoro-4-methoxy-phenyl)-amide]4-{[2-fluoro-4-(2-oxo-2H-pyridin-1-yl)-phenyl]-amide};

(R)-1-Methyl-4,6-dihydro-1H-pyrrolo[3,4-c]pyrazole-4, 5-dicarboxylic acid 5-[(4-chloro-phenyl)-amide]5-{[2,6-difluoro-4-(2-oxo-2H-pyridin-1-yl)-phenyl]-amide};

(R)-1-Methyl-4,6-dihydro-1H-pyrrolo[3,4-c]pyrazole-4, 5-dicarboxylic acid 5-[(5-chloro-pyridin-2-yl)-amide] 4-{[2-fluoro-4-(2-oxo-2H-pyrazin-1-yl)-phenyl]-amide};

and any pharmaceutically acceptable salt thereof.

20. A compound according to claim 1, selected from the group consisting of:

(R)-1-Methyl-4,6-dihydro-1H-pyrrolo[3,4-c]pyrazole-4, 5-dicarboxylic acid 4-{[2-fluoro-4-(3-oxo-morpholin-4-yl)-phenyl]-amide}5-[(4-methoxy-phenyl)-amide];

(R)-1-Methyl-4,6-dihydro-1H-pyrrolo[3,4-c]pyrazole-4, 5-dicarboxylic acid 5-[(5-chloro-pyridin-2-yl)-amide] 4-{[2-fluoro-4-(3-oxo-morpholin-4-yl)-phenyl]-amide}; and (R)-1-Methyl-4,6-dihydro-1H-pyrrolo[3,4-c]pyrazole-4, 5-dicarboxylic acid 5-[(3-fluoro-4-methoxy-phenyl)-amide]4-{[2-fluoro-4-(3-oxo-morpholin-4-yl)-phenyl]-amide};

and any pharmaceutically acceptable salt thereof.

* * * * *